(12) United States Patent
Park et al.

(10) Patent No.: US 11,859,184 B2
(45) Date of Patent: *Jan. 2, 2024

(54) MULTI-CONJUGATE OF SIRNA AND PREPARING METHOD THEREOF

(71) Applicant: KIP Co. Ltd., Daejeon (KR)

(72) Inventors: Tae Gwan Park; Hye Jung Mok, Daejeon (KR); Soo Hyeon Lee, Daejeon (KR)

(73) Assignee: Kip Co., Ltd., Daejeon (KR)

(*) Notice: Subject to any disclaimer, the term of this patent is extended or adjusted under 35 U.S.C. 154(b) by 0 days.

This patent is subject to a terminal disclaimer.

(21) Appl. No.: 17/945,842

(22) Filed: Sep. 15, 2022

(65) Prior Publication Data
US 2023/0070118 A1    Mar. 9, 2023

Related U.S. Application Data

(63) Continuation of application No. 17/811,686, filed on Jul. 11, 2022, now abandoned, which is a continuation of application No. 16/781,766, filed on Feb. 4, 2020, now abandoned, which is a continuation of application No. 16/040,795, filed on Jul. 20, 2018, now Pat. No. 10,597,659, which is a continuation of application No. 15/483,528, filed on Apr. 10, 2017, now abandoned, which is a continuation of application No. 14/312,530, filed on Jun. 23, 2014, now Pat. No. 9,644,209, which is a continuation of application No. 14/048,951, filed on Oct. 8, 2013, now Pat. No. 9,255,269, which is a continuation of application No. 12/514,306, filed as application No. PCT/KR2009/002252 on Apr. 29, 2009, now Pat. No. 8,580,946.

(51) Int. Cl.
  *C12N 15/113*    (2010.01)
  *C12N 15/11*     (2006.01)

(52) U.S. Cl.
  CPC ........ *C12N 15/1136* (2013.01); *C12N 15/111* (2013.01); *C12N 15/113* (2013.01); *C12N 2310/14* (2013.01); *C12N 2310/51* (2013.01)

(58) Field of Classification Search
  CPC . C12N 15/111; C12N 15/113; C12N 15/1136; C12N 2310/14; C12N 2310/51
  USPC ..................... 435/6.1, 91.1, 91.31, 455, 458; 514/44 A; 536/23.1, 24.5
  See application file for complete search history.

(56) References Cited

U.S. PATENT DOCUMENTS

| | | | |
|---|---|---|---|
| 5,552,535 A | 9/1996 | McLean et al. | |
| 8,106,173 B2 | 1/2012 | Kandimalla et al. | |
| 8,110,674 B2 | 2/2012 | Manoharan et al. | |
| 8,188,261 B2 | 5/2012 | Kandimalla et al. | |
| 8,362,233 B2 | 1/2013 | Kandimalla et al. | |
| 8,431,544 B1 | 4/2013 | Agrawal et al. | |
| 8,580,946 B2 | 11/2013 | Park et al. | |
| 8,759,310 B2 | 6/2014 | Kandimalla et al. | |
| 9,243,050 B2 | 1/2016 | Kandimalla et al. | |
| 9,255,269 B2 * | 2/2016 | Park ................... | C12N 15/1136 |
| 9,616,085 B2 | 4/2017 | Hong et al. | |
| 9,644,209 B2 * | 5/2017 | Park ..................... | C12N 15/111 |
| 10,597,659 B2 * | 3/2020 | Park ................... | C12N 15/1136 |
| 11,078,484 B2 | 8/2021 | Brown et al. | |
| 2004/0235773 A1 | 11/2004 | Zhao et al. | |
| 2007/0287681 A1 | 12/2007 | Jeong et al. | |
| 2008/0108801 A1 | 5/2008 | Manoharan et al. | |
| 2008/0214436 A1 | 9/2008 | Yu et al. | |
| 2008/0287383 A1 | 11/2008 | Quay et al. | |
| 2008/0311040 A1 | 12/2008 | Berry et al. | |
| 2009/0126038 A1 | 5/2009 | Van De craen et al. | |
| 2013/0064786 A1 | 3/2013 | Hong et al. | |
| 2013/0330293 A1 | 12/2013 | Long et al. | |
| 2014/0194610 A1 | 7/2014 | Verdine et al. | |
| 2014/0309281 A1 | 10/2014 | Park et al. | |
| 2015/0197754 A9 | 7/2015 | Park et al. | |
| 2015/0299695 A1 | 10/2015 | Uhlmann et al. | |

(Continued)

FOREIGN PATENT DOCUMENTS

| | | |
|---|---|---|
| CN | 114466929 A | 5/2022 |
| JP | 2014-527819 | 10/2014 |

(Continued)

OTHER PUBLICATIONS

Bolcato-Bellemin et al. (2007), "Sticky overhangs enhance siRNA-mediated gene silencing," Proc. Natl. Acad. Sci. USA, 104:41: 16050-16055.

Elbashir et al. (2001), "Duplexes of 21-nucleotide RNAs mediate RNA interference in cultured mammalian cells," Nature, 411: 494-498.

Gary et al. (2007), "Polymer-based siRNA delivery: Perspective on the fundamental and phenomenological distinctions from polymer-based DNA delivery," J. Controlled Release, 121: 64-73.

Jeong, J.H., et al., siRNA conjugate delivery systems. Bioconjug Chem. Jan. 2009;20(1):5-14. doi: 10.1021/bc800278e.

(Continued)

*Primary Examiner* — Jane J Zara
(74) *Attorney, Agent, or Firm* — Knobbe, Martens, Olson & Bear, LLP

(57) ABSTRACT

The present invention relates to a multi-conjugate of small interfering RNA (siRNA) and a preparing method of the same, more precisely a multi-conjugate of siRNA prepared by direct binding of double stranded sense/antisense siRNA monomers or indirect covalent bonding mediated by a cross-linking agent or a polymer, and a preparing method of the same. The preparing method of a siRNA multi-conjugate of the present invention is characterized by simple and efficient reaction and thereby the prepared siRNA multi-conjugate of the present invention has high molecular weight multiple times the conventional siRNA, so that it has high negative charge density, suggesting that it has excellent ionic interaction with a cationic gene carrier and high gene delivery efficiency.

10 Claims, 9 Drawing Sheets

Specification includes a Sequence Listing.

(56) References Cited

U.S. PATENT DOCUMENTS

| | | |
|---|---|---|
| 2015/0315585 A1 | 11/2015 | Uhlmann et al. |
| 2016/0193354 A1 | 7/2016 | Noe et al. |
| 2016/0298124 A1 | 10/2016 | Borodovsky et al. |
| 2016/0347780 A1 | 12/2016 | Wada et al. |
| 2017/0189525 A1 | 7/2017 | Brunskill et al. |
| 2017/0204408 A9 | 7/2017 | Lewis et al. |
| 2017/0349896 A1 | 12/2017 | Albaek et al. |
| 2018/0080028 A1 | 3/2018 | Park et al. |
| 2018/0312839 A1 | 11/2018 | Bhat et al. |
| 2019/0062743 A1 | 2/2019 | Uhlmann et al. |
| 2019/0085331 A1 | 3/2019 | Hadwiger et al. |
| 2020/0239892 A1 | 7/2020 | Park et al. |
| 2020/0308578 A1 | 10/2020 | Woolf et al. |
| 2021/0380979 A1 | 12/2021 | Brown et al. |
| 2022/0290148 A1 | 9/2022 | Hadwiger et al. |
| 2023/0114023 A1 | 4/2023 | Brown et al. |

FOREIGN PATENT DOCUMENTS

| | | |
|---|---|---|
| JP | 2017-565893 A | 7/2018 |
| JP | 2011-518784 | 10/2019 |
| KR | 10-2011-0083919 A | 7/2011 |
| WO | WO 2004/030634 A2 | 4/2004 |
| WO | WO 2004/090108 A2 | 10/2004 |
| WO | WO 2004/091515 A2 | 10/2004 |
| WO | WO 2004/094345 A2 | 11/2004 |
| WO | WO 2004/094595 A2 | 11/2004 |
| WO | WO 2007/117686 A2 | 10/2007 |
| WO | WO 2008/109105 A2 | 9/2008 |
| WO | WO 2009/014887 A2 | 1/2009 |
| WO | WO 2009/126933 A2 | 10/2009 |
| WO | WO2010/021720 A1 | 2/2010 |
| WO | WO 2011/031520 A1 | 3/2011 |
| WO | WO 2011/109380 A1 | 9/2011 |
| WO | WO 2013/040429 A1 | 3/2013 |
| WO | WO 2014/043544 A1 | 3/2014 |
| WO | WO 2014/208973 | 12/2014 |
| WO | WO 2019/105421 A1 | 6/2019 |
| WO | WO 2021/021959 A2 | 2/2021 |
| WO | WO 2021/236689 A1 | 11/2021 |

OTHER PUBLICATIONS

Kim, S.H., et al., Local and systemic delivery of VEGF siRNA using polyelectrolyte complex micelles for effective treatment of cancer. J Control Release. Jul. 14, 2008;129(2): 107-16. doi: 10.1016/j.jconrel.2008.03.008. Epub Mar. 14, 2008.

Kim, S.H., et al., LHRH receptor-mediated delivery of siRNA using polyelectrolyte complex micelles self-assembled rom siRNA-PEG-LHRH conjugate and PEI. Bioconjug Chem. Nov. 19, 2008;19(11):2156-62. doi: 10.1021/bc800249n.

Mok et al., "Self-crosslinked and reducible fusogenic peptides for intracellular delivery of siRNA", Biopolymers. J008 Ocl;89(10):881-8. doi: 10.1002/bip.21032.

Mok et al., "Multimeric small interfering ribonucleic acid for highly efficient sequence-specific gene silencing", Natural Materials, vol. 9(3):272-278 (2010).

Moschos, S.A, et al., Lung delivery studies using siRNA conjugated to TAT(48-60) and penetralin reveal peptide nduced reduction in gene expression and induction of innate immunity. Bioconjug Chem. Sep. 2007-Ocl;18(5):1450-9. Epub Aug. 21, 2007.

Muratovska, A., et al., Conjugate for efficient delivery of short interfering RNA (siRNA) into mammalian cells. FEBS Lett. Jan. 30, 2004;558(1-3):63-8.

Office Action issued in U.S. Appl. No. 12/514,306 dated Oct. 6, 2011.

Office Action in U.S. Appl. No. 12/514,306 dated Jan. 6, 2012, 7 pages.

Notice of Allowance in U.S. Appl. No. 12/514,306 dated Jul. 8, 2013, 8 pages.

U.S. Office Action for U.S. Appl. No. 14/081,951 dated Sep. 26, 2014.

Notice of Allowance in U.S. Appl. No. 16/040,795 dated Nov. 6, 2019, 5 pages.

Extended European Search Report for Application No. 09731474.4, dated Jul. 18, 2012, in 5 pages.

International Search Report and Written Opinion for Application No. PCT/KR2009/002252, dated Apr. 13, 2010, in 23 pages.

Extended Search Report for Application No. 17150172.9, dated Apr. 6, 2017, in 7 pages.

Bonger, K. M., "Dimeric ligands for GPCRs involved in human reproduction: synthesis and biological evaluation" pp. 1-217, Dec. 19, 2008.

Brown, JM et al., Ligan Conjugated Multimeric siRNAs Enable Enhanced Uptake and Multiplexed Gene Silencing. Nucieic Acid Therapeutics, Sep. 26, 2019, vol. 29, No. 5, pp. 231-244; entire document. DOI: 10.1089/nat.2019.0782.

Cellamare et al., "Design, synthesis, and biological evaluation of glycine-based molecular tongs as inhibitors of AB1-40 aggregation in vitro", Bioorganic & Medicinal Chemistry, vol. 16, 2008, pp. 4810-4822.

Hong et al, Gene Silencing by siRNA Microhydrogels via Polymeric Nanoscale Condensation, Aug. 2011, JAGS, 133: 13914-13917.

Kang et al. "HER2 RNA Aptamerand Cell Penetrating Peptide-Mediated Delivery of Multimeric Antisense Strands of siRNAs for Gene Silencing: Multimeric antisense strands of siRNAS", bull. Korean chem. Soc., vol. 37, No. 9, Aug. 29, 2016, pp. 1440-1444, XPO55746857, ISSN: 1229-5949, DOI: 10.1002/bkcs.10886.

Kashihara et al, "Analysis of Renal Microcirculation and Permeability-Change with Bio-Imaging Techniques", Kenbikyo, 2011, vol. 46, No. 3, p. 181-187.

Kim et al. (2006) "PEG conjugated VEGF siRNA for anti-angiogenic gene therapy," Journal of Controlled Release, 116:123-129.

Lee, Soo Hyeon, et al. "Dual gene targeted multimeric siRNA for combinatorial gene silencing." Biomaterials, vol. 32, No. 9, Oct. 23, 2010, pp. 2359-2368.

Lee et al., (2012) "Molecularly Self-Assembled Nucleic-Acid Nanoparticles for Targeted in Vivo siRNA Delivery," Nature Nanotechnology, 7(6):389-393.

Lee et al., (2012) "Small-Interfering RNA (siRNA)-Based Functional Micro-and Nanostructures for Efficient and Selective Gene Silencing," Accounts of Chemical Research, 45(7):1014-1025.

Motoyashi et al., "Glomerular Disease and tubule injury", Japanese Journal of Pediatric Nephrology, 2009, vol. 22, No. 2, p. 76-81.

Rinsho Yakuri, Japanese Journal of Clinical Pharmacology and Therapeutics, 2016, vol. 47, No. 2, p. 56-61.

Schiffelers RM, et al. "Cancer siRNA therapy by tumor selective delivery with ligand-targeted sterically stabilized nanoparticle", Nucleic Acids Res. 32 (2004) e149. Published Oct. 1, 2004.

Sugo, T. et al., Development of antibody-siRNA conjugate targeted to cardiac and skeletal muscles, Journal of Controlled Release, 237 (2016) 1-13.

Sun et al., (1997) "Synthesis of 3'-thioribonucleosides and their incorporation into oligoribonucleotides via phosphoramidite chemistry," RNA, 3(11):1352-63.

Tai, Wanyi, Bin Qin, and Kun Cheng. "Inhibition of breast cancer cell growth and invasiveness by dual silencing of HER-2 and VEGF." Molecular pharmaceutics 7.2 (2010): 543-556.

Xu, et al., "Delivery systems for siRNA drug development in cancer therapy", Asian Journal of Pharmaceutical Sciences, Aug. 28, 2014, vol. 10, No. 1, pp. 1-12.

Yoo et al., "Multivalent comb-type aptamer-siRNA conjugates for efficient and selective intracellular delivery", Chemical Communications, vol. 50, No. 51, May 8, 2014, pp. 6765-6767, XP055747253.

Zhang et al., "Synthesis and Biological Evaluation of Bivalent Ligands for the Cannabinoid 1 Receptor" Journal of Medicinal Chemistry, 53, pp. 7048-7060.

Office Action in U.S. Appl. No. 14/048,951 dated Sep. 26, 2014, 10 pages.

Final Office Action in U.S. Appl. No. 14/048,951 dated Jun. 16, 2015, 7 pages.

(56) References Cited

OTHER PUBLICATIONS

Office Action in U.S. Appl. No. 14/312,530 dated Mar. 2, 2016, 6 pages.
Notice of Abandonment in U.S. Appl. No. 12/514,306 dated Jul. 17, 2012, 2 pages.
Final Office Action in U.S. Appl. No. 14/312,530 dated Oct. 17, 2016, 10 pages.
Office Action in U.S. Appl. No. 16/040,795 dated Jul. 11, 2019, 7 pages.
Notice of Allowance in U.S. Appl. No. 14/048,951 dated Oct. 5, 2015, 5 pages.
Notice of Allowance in U.S. Appl. No. 14/312,530 dated Feb. 3, 2017, 6 pages.
Notice of Abandonment in U.S. Appl. No. 15/483,528 dated Oct. 29, 2018, 2 pages.
Office Action for Application No. 17150172.9, dated Apr. 6, 2022, in 3 pages.
International Search Report and Written Opinion for International Application No. PCT/US21/55085, dated Feb. 1, 2022, in 14 pages.
Notice of Abandonment in U.S. Appl. No. 17/811,686, dated May 16, 2023, in 2 pages.

* cited by examiner ical distinctions from polymer-based DNA delivery. *J Control Release* 121, 64-73).

SEQUENCE LISTING

```
Sequence total quantity: 1
SEQ ID NO: 1            moltype = AA  length = 30
FEATURE                 Location/Qualifiers
REGION                  1..30
                        note = cationic fusogenic peptide
source                  1..30
                        mol_type = protein
                        organism = synthetic construct
SEQUENCE: 1
WEAKLAKALA KALAKHLAKA LAKALAACEA                                                30
```

MULTI-CONJUGATE OF SIRNA AND PREPARING METHOD THEREOF

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

SEQUENCE LISTING IN ELECTRONIC FORMAT

The present application includes a Sequence Listing which has been submitted electronically in ASCII format and is hereby incorporated herein by reference in its entirety. The Electronic Sequence Listing is provided as a file entitled MPEG002SEQLIST.txt, created and last saved on Feb. 3, 2020, which is 844 bytes in size, which is replaced by a Replacement Electronic Sequence Listing submitted in XML format herewith as a file entitled MPEG002C7ReplacementSeqListing.xml, which is 2,324 bytes in size and was created on Aug. 30, 2023.

BACKGROUND

Technical Field

The present invention relates to a multi-conjugate of siRNA (small interfering RNA) and a preparing method of the same, more precisely a multi-conjugate of siRNA prepared by direct or indirect covalent bonding of double-stranded sense/antisense siRNA monomers mediated by a cross-linking agent or a polymer.

Background Art

SiRNA (small interfering RNA) is a short double-stranded RNA composed of 19-22 nucleic acids, which targets mRNA (messenger RNA) of a gene whose nucleotide sequence is identical with its sense strand in order to suppress expression of the gene by decomposing the target gene (Elbashir, S. M., Harborth, J., Lendeckel, W., Yalcin, A., Weber, K., and Tuschl, T. (2001) Duplexes of 21-nucleotide RNAs mediate RNA interference in cultured mammalian cells. *Nature* 411, 494-8).

SiRNA is capable of inhibiting gene expression even with 10 times less amount than the required amount of conventional antisense oligonucleotide, suggesting that it has excellent gene selectivity indicating that it is highly capable of inhibiting a target gene alone. However, siRNA is so unstable in vivo that it is easily decomposed within a short period of time and it is anionic which makes cell membrane transmission difficult, resulting in low intracellular delivery efficiency.

To increase siRNA delivery efficiency, a nano-sized ion-complex is generally used which is prepared by ionic bonding of siRNA and diverse functional cationic polymers, lipids or cationic peptides. However, the conventional siRNA has the molecular weight of about 15,000 and has a very stiff structure of double strand. So, it is very difficult to prepare a stable siRNA/cationic gene carrier complex (Gary, D. J., Puri, N., and Won, Y. Y. (2007) Polymer-based siRNA delivery: perspectives on the fundamental and phenomenological distinctions from polymer-based DNA delivery. *J Control Release* 121, 64-73).

Therefore, studies have been actively undergoing to prepare a stable siRNA complex with a gene carrier. It has been attempted to increase charge density of each element of an siRNA or a cationic carrier to increase stability of an ionic complex. As an example, it has been attempted to induce strong ionic interaction by increasing molecular weight of cationic polymer or lipid or by introducing a strong cationic group into a cationic carrier. However, even if the said method can increase gene delivery efficiency, it also increases non-specific cytotoxicity owing to the strong cations of a gene carrier, making the clinical application difficult. So, a new approach has recently been made to modify siRNA itself to produce a stable complex with the conventional gene carrier.

According to recent reports, 4-8 additional nucleotides (deoxythymine, deoxyadenine) are added to sense strand in order to increase the molecular weight of siRNA, resulting in complementary base pairing in siRNA complex (Bolcato-Bellemin, A. L., Bonnet, M. E., Creusat, G., Erbacher, P., and Behr, J. P. (2007) Sticky overhangs enhance siRNA-mediated gene silencing. *Proc Natl Acad Sci USA* 104, 16050-5). However, at this time, complementary bindings of 4-8 nucleotides are so unstable that it cannot be confirmed by electrophoresis.

Thus, the present inventors continued study to increase stability and delivery efficiency of siRNA. As a result, the present inventors completed this invention by confirming that a multi-conjugate of siRNA prepared by direct or indirect covalent bonding of double-stranded sense/antisense siRNA monomers mediated by a cross-linking agent or a polymer has excellent gene delivery efficiency owing to strong ionic bond with a cationic gene carrier and does not induce severe immune response, compared with the conventional siRNA, so that it can be effectively used for gene therapy.

SUMMARY

Technical Problem

It is an object of the present invention to provide a multi-conjugate of siRNA having higher gene inhibition efficiency than the conventional siRNA.

It is another object of the present invention to provide a simple but highly efficient preparing method of a multi-conjugate of siRNA that is capable of binding stably with a gene carrier owing to the high negative-charge density.

Technical Solution

To achieve the above objects, the present invention provides a multi-conjugate of siRNA having the following structure of [Structural Formula I] or [Structure Formula II] prepared by direct or indirect covalent bonding of double-stranded sense/antisense siRNA monomers mediated by a cross-linking agent or a polymer:

$$(-X-A-)_n \qquad \text{[Structural Formula I]}$$

(wherein,

X is double-stranded siRNA monomer;

A is either presented or not presented, a cross-linking agent or a polymer; and n is the number of double-stranded siRNA monomer), $$x\text{-}A\text{-}(X\text{-}A\text{-})_n\text{-}x' \qquad \text{[Structural Formula II]}$$

(wherein,
X is double-stranded siRNA monomer;
x or x' is single-stranded siRNA monomer
A is either presented or not presented, a cross-linking agent or a polymer; and
n is the number of double-stranded siRNA monomer).

The present invention also provides a preparing method of a multi-conjugate of siRNA having the structure of [Structural Formula I] or [Structural Formula II] containing the step of direct or indirect covalent bonding of double-stranded sense/antisense siRNA monomers mediated by a cross-linking agent or a polymer.

The present invention further provides an ionic complex formed by ionic interaction between the said siRNA multi-conjugate and a cationic gene carrier selected from the group consisting of cationic peptides, cationic lipids and cationic polymers.

The present invention also provides a method for treating cancer or angiogenesis related disease containing the step of administering the said ionic complex to a subject.

In addition, the present invention provides a use of the said ionic complex for the production of an anticancer agent or a therapeutic agent for angiogenesis related disease.

Hereinafter, the present invention is described in detail.

DETAILED DESCRIPTION

The present invention provides a multi-conjugate of siRNA having the following structure of [Structural Formula I] or [Structure Formula II] prepared by direct or indirect covalent bonding of double-stranded sense/antisense siRNA monomers mediated by a cross-linking agent or a polymer:

   [Structural Formula I]

(wherein,
X is double-stranded siRNA monomer;
A is either presented or not presented, a cross-linking agent or a polymer; and
n is the number of double-stranded siRNA monomer),

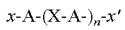   [Structural Formula II]

(wherein,
X is double-stranded siRNA monomer;
x or x' is single-stranded siRNA monomer
A is either presented or not presented, a cross-linking agent or a polymer; and
n is the number of double-stranded siRNA monomer).

In this invention, the said double-stranded sense/antisense siRNA monomer preferably has 15-50 nucleotides and more preferably has 15-29 nucleotides, but not always limited thereto.

In this invention, the number of the said double-stranded sense/antisense siRNA monomer is preferably 1-150 and more preferably 1-100, but not always limited thereto.

The multi-conjugate of siRNA of the present invention is preferably prepared by the following two methods, but not always limited thereto:

1) The first method: single-stranded sense siRNA and antisense siRNA each having a functional group at terminal are reacted respectively in the presence of a cross-linking agent or a polymer to produce single-stranded sense and antisense siRNA dimers. Each dimer is complementarily annealed in aqueous solution (see FIGS. 1B and 1D).

Particularly, sense strand siRNA and antisense strand siRNA each having sulfhydryl group substituted at terminal are reacted to produce dimers by cleavable or non-cleavable covalent bond using DIME (Dithio-bis-maleimidoethane) or BM(PEG)$_2$ (1,8-bis(maleimido)diethylene glycol), the cross-linking agent reactable with sulfhydryl group. Then, equal amount of each dimer is loaded in PBS to induce complementary binding via hydrogen bond, resulting in the preparation of a siRNA multi-conjugate.

2) The second method: double-stranded siRNA (prepared by complementary hydrogen bond) having a functional group substituted at terminal proceeds to covalent bond mediated by a cross-linking agent or a polymer, resulting in the preparation of a siRNA multi-conjugate (see FIGS. 1A and 1C).

Particularly, single-stranded siRNA introduced with sulfhydryl group at terminal proceeds to complementary hydrogen bond, and the resultant product proceeds to covalent bond based on oxidation in the presence of a cross-linking agent or DMSO, resulting in the preparation of a siRNA multi-conjugate.

In the production of the said multi-conjugate of siRNA, the molecular weight of siRNA oligo-strand is preferably selected in the range from 10,000-50,000, but not always limited thereto. The siRNA for the present invention is not limited and any one that is being used for treatment or study can be accepted, for example any siRNA that is being used for gene therapy or study or is expected to be used in near future is selected, which is exemplified by c-myc, c-myb, c-fos, c-jun, bcl-2 or VEGF, VEGF-B, VEGF-C, VEGF-D, PIGF, etc.

Hydroxy group (—OH) at terminal of the said siRNA can be substituted with a functional group such as sulfhydryl group (—SH), carboxyl group (—COOH) or amine group (—NH$_2$).

The substitution can be performed at 3'end or 5'end, and is preferably occurred at 3' ends of both sense and antisense are substituted with such functional group, but not always limited thereto.

The polymer herein can be a non-ionic hydrophilic polymer such as polyethyleneglycol (PEG), polyvinylpyrolidone and polyoxazolin, or a hydrophobic polymer such as PLGA and PLA, etc.

The cross-linking agent herein has the molecular weight of 100-10000, which is exemplified by DTME (Dithio-bis-maleimidoethane), BM(PEG)$_2$ (1,8-Bis-maleimidodiethyleneglycol), maleimide, NHS (N-hydroxysuccinimide), vinylsulfone, iodoacetyl, nitrophenyl azide, isocyanate, pyridyldisulfide, hydrazide or hydroxyphenyl azide, but not always limited thereto.

Either the cross-linking agent having external stimulus-mediated cleavable bonds or the cross-linking agent having non-cleavable bonds can be used herein, for example, the cross-linking agent of the present invention can have non-cleavable bond such as amide bond and urethane bond, and cleavable bond such as acid cleavable bond (covalent bond of ester, hydrazone, acethal, etc) and reductant cleavable bond (disulfide bond), etc. And additionally, any cross-linking agent available for drug modification can be used without limitation.

The said multi-conjugate of siRNA can include cell selective ligand at the end.

The ligand can be selected from the group consisting of cell specific antibody, cell selective peptide, cell growth factor, folic acid, galactose, mannose, RGD, and transferrin. Such ligand can be introduced at the end of the multi-conjugate by disulfide bond, amide bond, or ester bond, etc.

The multi-conjugate of siRNA of the present invention can form an ionic complex by ionic interaction with a cationic gene carrier (cationic lipid, cationic polymer, cationic peptide, etc).

The cationic peptide is KALA (cationic fusogenic peptide), polylysine, polyglutamic acid or protamine. The KALA preferably has the peptide sequence of WEAKLAKALAKALAKHLAKALAKALAACEA (SEQ. ID. NO: 1), but not always limited thereto.

The cationic lipid is dioleyl phosphatidylethanolamine or cholesterol dioleyl phosphatidylcholine.

The cationic polymer is polyethyleneimine, polyamine or polyvinylamine

To investigate target gene inhibition efficiency of the multi-conjugate of siRNA of the present invention, the inventors mixed siRNA with the gene carrier Linear PEI to prepare an ionic complex, which was then treated to cancer cells expressing GFP stably. Then, GFP level was measured using fluorophotometer. As a result, the multi-conjugate of siRNA of the present invention demonstrated higher gene delivery efficiency using a cationic gene carrier than conventional siRNA, suggesting that the multi-conjugate of siRNA of the present invention had excellent target gene inhibition efficiency (see FIG. 4).

To investigate binding force with a cationic gene carrier and stability of the siRNA multi-conjugate of the present invention, the inventors produced an ionic complex by mixing the gene carrier Linear PEI and siRNA, followed by observation of shape and size using Atomic Force Microscopy (AFM). As a result, compared with conventional siRNA, the siRNA multi-conjugate of the present invention demonstrated excellent binding force with a cationic polymer and had smaller size which favored production of even and small nano particles (see FIG. 5).

To investigate the amount of a cationic polymer conjugated to the siRNA multi-conjugate of the present invention, gel retardation assay was performed. As a result, compared with conventional siRNA, the siRNA multi-conjugate of the present invention demonstrated higher charge density, which favored production of an ionic complex by binding a cationic polymer even at a low concentration (see FIG. 6).

The present inventors also investigated gene inhibition efficiency of the siRNA multi-conjugate of the present invention. To do so, the inventors produced an ionic complex by mixing the gene carrier Linear PEI with siRNA, which was treated to cancer cells. Then, VEGF level was measured by ELISA. As a result, compared with conventional siRNA, the siRNA multi-conjugate of the present invention formed an ionic complex with a cationic polymer more stably and evenly, suggesting that the multi-conjugate of siRNA of the present invention had excellent gene delivery efficiency and excellent selective inhibition of a target gene (see FIG. 7).

The present inventors also investigated gene inhibition efficiency of the siRNA multi-conjugate of the present invention according to the molecular weight. First, siRNA was separated over the size by gel separation method. Each separated siRNA was mixed with Linear PEI to produce an ionic complex. Then, the complex was treated to cancer cells, followed by quantification of VEGF by ELISA. As a result, as the molecular weight of the siRNA multi-conjugate of the present invention was increased, charge density was increased, and accordingly the efficiency of gene delivery using a cationic polymer was also increased (see FIG. 8).

The present inventors also investigated immune response inducing ability of the siRNA multi-conjugate of the present invention. The present inventors produced an ionic complex by mixing the cationic gene carrier Linear PEI, jet PEI or DOTAP with siRNA, which was treated to human PBMC. Then, Interferon-α (INF-α) was quantified by ELISA. As a result, there was no significant induction of INF-α by the siRNA multi-conjugate of the present invention (see FIG. 9A).

To investigate immune response inducing capacity of the siRNA multi-conjugate of the present invention, the inventors produced an ionic complex by mixing the cationic gene carrier Linear PEI with siRNA, which was intravenously injected to ICR mouse at 7 weeks. Blood was taken from the heart of the mouse, followed by quantification of blood siRNA by ELISA. As a result, in this animal model, there was no significant induction of INF-α by the siRNA multi-conjugate of the present invention, compared with conventional siRNA (see FIG. 9B).

Therefore, the siRNA multi-conjugate of the present invention was confirmed to have higher molecular weight, higher negative charge density, higher stability, and higher ionic strength with a cationic gene carrier than conventional siRNA, resulting in high gene delivery efficiency. The siRNA multi-conjugate of the present invention can be simply produced by using the therapeutic gene siRNA alone, which favors biocompatibility. Moreover, even as multi-conjugate form, the siRNA of the present invention maintains gene inhibition activity but has increased gene delivery efficiency, suggesting that it has higher intracellular introduction efficiency and thus higher gene inhibition effect than conventional siRNA.

VEGF binds to VEGF receptor existing on vascular endothelial cell surface and is then functioning to accelerate growth and migration of endothelial cell and angiogenesis. In particular, tumor growth and metastasis are closely related to angiogenesis. So, inhibition of angiogenesis can be a new approach to treat cancer by inhibiting the growth of tumor. The siRNA multi-conjugate of the present invention can inhibit VEGF significantly, so that it can be effectively used for treating cancer.

The present invention also provides a preparing method of a multi-conjugate of siRNA having the structure of [Structure Formula I] or [Structure Formula II] containing the step of direct or indirect covalent bonding of double-stranded sense/antisense siRNA monomers mediated by a cross-linking agent or a polymer.

In a preferred embodiment of the present invention, the preparing method of the multi-conjugate of siRNA is composed of the following steps:
1) preparing yXy by complementary hydrogen bonding of single-stranded sense/antisense siRNA monomers (yx+ x'y) having substitutions with same functional groups at the ends; and
2) inducing covalent bond of the yXy mediated by a cross-linking agent or a polymer (Herein, X is double-stranded siRNA monomer, x and x' are single-stranded sense/antisense siRNA monomers, and y is the functional group introduced in the end.).

In another preferred embodiment of the present invention, the preparing method of the multi-conjugate of siRNA is composed of the following steps:
1) preparing dimers of xyyx and x'yyx' by covalent bonding of single-stranded sense/antisense siRNA monomers (yx and x'y) having substitutions with same functional groups at the ends; and
2) inducing complementary hydrogen bond between the dimers xyyx and x'yyx' (Herein, X is double-stranded siRNA monomer, x and x' are single-stranded sense/antisense siRNA monomers, and y is the functional group introduced in the end.).

In another preferred embodiment of the present invention, the preparing method of the multi-conjugate of siRNA is composed of the following steps:
1) preparing yXz by complementary hydrogen bonding of single-stranded sense/antisense siRNA monomers (yx+ x'z) having substitutions with different functional groups at the ends; and
2) inducing covalent bond of the yXz mediated by a cross-linking agent or a polymer (Herein, X is double-stranded siRNA monomer, x and x' are single-stranded sense/antisense siRNA monomers, and y and z are the functional groups introduced in the ends.).

In another preferred embodiment of the present invention, the preparing method of the multi-conjugate of siRNA is composed of the following steps:
1) preparing dimers of xyzx and x'yzx' by covalent bonding of single-stranded sense/antisense siRNA monomers (yx and xz, x'y and x'z) having substitutions with different functional groups at the ends; and
2) inducing complementary hydrogen bond between the dimers xyzx and x'yzx' (Herein, X is double-stranded siRNA monomer, x and x' are single-stranded sense/antisense siRNA monomers, and y and z are the functional groups introduced in the ends.).

In the preparing method of a multi-conjugate of siRNA of the present invention, siRNA oligo strand is preferably selected from those having the molecular weight of 10,000-50,000. The siRNA herein is not limited and any siRNA that is used for treatment or study can be accepted, for example any siRNA that has been used for gene therapy or study or is expected to be used for that purpose can be accepted, which is exemplified by c-myc, c-myb, c-fos, c-jun, bcl-2 or VEGF, VEGF-B, VEGF-C, VEGF-D, PIGF, etc.

In the preparing method of a multi-conjugate of siRNA of the present invention, the covalent bond is preferably selected from the group consisting of non-cleavable bonds (amide bond and urethane bond), acid cleavable bonds (ester bond, hydrazone bond and acethal bond), reductant cleavable bond (disulfide bond), bio-cleavable bonds and enzyme cleavable bonds, but not always limited thereto.

In the preparing method of a multi-conjugate of siRNA of the present invention, hydroxyl group (—OH) at the end of the single-stranded sense/antisense siRNA monomer is preferably substituted with one of the functional groups selected from the group consisting of sulfhydryl group (—SH), carboxyl group (—COOH) and amine group (—NH$_2$), but not always limited thereto.

The substitution is preferably performed at 3' end or 5' end, and it is preferred that sense and antisense are substituted with functional groups at 3' ends, but not always limited thereto.

In the preparing method of a multi-conjugate of siRNA of the present invention, the polymer used as a mediator for covalent bond is preferably one or more non-ionic hydrophilic polymers selected from the group consisting of PEG, Pluronic, polyvinylpyrolidone and polyoxazolin; or one or more biocleavable polyester polymers selected from the group consisting of poly-L-lactic acid, poly-glycolic acid, poly-D-lactic-co-glycolic acid, poly-L-lactic-co-glycolic acid, poly-D,L-lactic-co-glycolic acid, polycaprolactone, polyvalerolactone, polyhydroxybutyrate and polyhydroxyvalerate, but not always limited thereto.

In the preparing method of a multi-conjugate of siRNA of the present invention, the cross-linking agent is one or more compounds having the molecular weight of 100-10,000, which is preferably selected from the group consisting of DIME (Dithio-bis-maleimidoethane), BM(PEG)$_2$ (1,8-Bis-maleimidodiethyleneglycol), maleimide, NHS (N-hydroxysuccinimide), vinylsulfone, iodoacetyl, nitrophenyl azide, isocyanate, pyridyldisulfide, hydrazide and hydroxyphenyl azide, but not always limits thereto.

In the preparing method of a multi-conjugate of siRNA of the present invention, the cell selective ligand is preferably added to the end of the said siRNA multi-conjugate, but not always limited thereto.

The said ligand is one or more compounds preferably selected from the group consisting of cell specific antibody, cell selective peptide, cell growth factor, folic acid, galactose, mannose, RGD and transferrin, but not always limited thereto.

In the preparing method of a multi-conjugate of siRNA of the present invention, the step of activating the functional group of the said siRNA can be additionally included, but not always limited thereto.

The material used for the activation of the functional group of the said siRNA is one or more compounds preferably selected from the group consisting of 1-ethyl-3,3-dimethylaminopropyl carbodiimide, imidazole, N-hydroxysuccinimide, dichlorohexylcarbodiimide, N-β-Maleimidopropionic acid, N-β-maleimidopropyl succinimide ester and N-Succinimidyl 3-(2-pyridyldithio)propionate, but not always limited thereto.

In the preparing method of a multi-conjugate of siRNA of the present invention, the preparation reaction is not limited, but generally performed at room temperature for about 24-48 hours. Ratio of each reactant added to the reaction is not limited and the length of siRNA multi-conjugate can be regulated by adjusting molar ratio (%) of a cross-linking agent to siRNA.

The aqueous solution used for complementary binding in this invention is PBS, Tris buffer or HEPES buffer, and more preferably the buffer having salt concentration of at least 100 mM.

The present invention also provides an ionic complex facilitating cellular transduction, which is formed by ionic interaction between the said siRNA multi-conjugate and a cationic gene carrier selected from the group consisting of cationic peptides, cationic lipids and cationic polymers.

An ionic complex can be prepared by ionic interaction between the siRNA multi-conjugate of the present invention and a cationic gene carrier. The said ionic complex is a small complex formed by interaction between an anionic gene and a polymer having counter ions (ex, cationic material), which is preferably 100-200 nm in size, but not always limited thereto.

In this invention, the cationic peptide is preferably selected from the group consisting of KALA (cationic fusogenic peptide), polylysine, polyglutamic acid and protamine, but not always limited thereto.

In this invention, the cationic lipid is preferably selected from the group consisting of dioleyl phosphatidylethanolamine and cholesterol dioleyl phosphatidyl choline, but not always limited thereto.

In this invention, the cationic polymer is preferably selected from the group consisting of polyethylenimine, polyamines and polyvinylamine, but not always limited thereto.

In the preparation of the ionic complex, the siRNA multi-conjugate of the present invention is diluted in PBS, to which a cationic substance is added. Then, the mixture stands at room temperature, resulting in the preparation of an ionic complex in aqueous solution. At this time, the content of the cationic substance is regulated by adjusting the ratio of positive charge of the cationic substance to negative charge of the siRNA to 1:1 (+/−=1/1)~100:1.

The present invention also provides a method for treating cancer or angiogenesis related disease containing the step of administering the said ionic complex to a subject.

In addition, the present invention provides a use of the said ionic complex for the production of an anticancer agent or a therapeutic agent for angiogenesis related disease.

The term "subject" herein indicates human or animals including monkey, dog, goat, pig and mouse that have cancer or angiogenesis related disease that can be improved by the administration of the ionic complex of the present invention.

The term "administration" herein indicates providing a required amount of the ionic complex of the present invention to a subject through a proper method.

The term "treatment" herein indicates all behavior performed to improve or relieving symptoms of cancer or angiogenesis related disease by administering the ionic complex of the present invention.

The cancer herein is preferably selected from the group consisting of breast cancer, colorectal cancer, rectal cancer, non-small cell lung cancer, non-Hodgkin's lymphoma (NHL), renal cell cancer, prostate cancer, liver cancer, pancreatic cancer, soft-tissue sarcoma, kaposi's sarcoma, carcinoid carcinoma, head and neck cancer, melanoma, ovarian cancer, mesothelioma and multiple myeloma, but not always limited thereto.

The angiogenesis related disease herein is selected from the group consisting of hemangioma, angiofibroma, arthritis, diabetic retinosis, retrolental fibroplasia, neovascular glaucoma, neovascular corneal disease, macular degeneration, macular dystrophy, pterygium, retinal degeneration, retrolental fibroplasia, trachoma, psoriasis, capillarectasia, granuloma pyogenicum, dermatitis seborrheica and acne, but not always limited thereto.

The siRNA multi-conjugate of the present invention is prepared by siRNA alone, so that it has excellent biocompatibility and excellent stability and improved binding capacity with various gene carriers without reducing gene inhibition activity of siRNA, suggesting that the siRNA multi-conjugate of the present invention has higher gene inhibition activity than conventional siRNA.

In this invention, an ionic complex prepared by mixing a siRNA multi-conjugate and the representative gene carrier Linear PEI was treated to cancer cells. As a result, significant VEGF inhibition effect was demonstrated, compared with conventional siRNA. That is, the siRNA multi-conjugate of the present invention forms a very stable and regular ionic complex with a cationic polymer and therefore the conjugate demonstrates excellent gene delivery effect and target gene inhibition effect.

Therefore, the ionic complex of the present invention can be used for diverse gene therapy, because the siRNA multi-conjugate can include diverse siRNA, in particular for gene therapy for cancer or angiogenesis related disease.

Advantageous Effect

The preparing method of a multi-conjugate of siRNA of the present invention is characterized by simple reaction process and high efficiency. Therefore, the siRNA multi-conjugate prepared by the above method has the molecular weight of multiple times the conventional siRNA, and thus has higher negative charge density, indicating that the siRNA multi-conjugate of the present invention has significantly high gene delivery efficiency resulted from excellent ionic interaction with a cationic gene carrier.

BRIEF DESCRIPTION OF THE DRAWINGS

The application of the preferred embodiments of the present invention is best understood with reference to the accompanying drawings, wherein:

FIG. 1A: Double-stranded siRNA having functional groups introduced in both ends is prepared by complementary base-pairing via hydrogen bonding of single-stranded sense siRNA and single-stranded antisense siRNA having same functional group substituted at one end. Then, a multi-conjugate of siRNA is prepared by covalent bonding using a cross-linking agent or a polymer. FIG. 1B: Dimer form of sense strand and antisense strand siRNA is first prepared by covalent bonding single-stranded sense siRNA and single-stranded antisense siRNA having same functional group substituted at one end using a cross-linking agent or a polymer. Then, a multi-conjugate of siRNA is prepared by complementary hydrogen bonding of each oligonucleotide. FIG. 1C Double-stranded siRNA having different functional groups introduced in both ends is prepared by complementary base-pairing via hydrogen bonding of single-stranded sense siRNA and single-stranded antisense siRNA having different functional group at each end. Then, a multi-conjugate of siRNA is prepared by direct covalent bonding or covalent bonding mediated by a cross-linking agent. FIG. 1D Dimer form of sense strand and antisense strand siRNA is first prepared by direct covalent bonding of single-stranded sense siRNA and single-stranded antisense siRNA having different functional group at each end or covalent bonding mediated by a cross-linking agent. Then, a multi-conjugate of siRNA is prepared by complementary base-pairing via hydrogen bonding of each oligonucleotide.

FIG. 7C illustrates the result of quantification of mRNA by RT-PCR to investigate gene inhibition efficiency.

FIG. 9A illustrates that an ionic complex is prepared by using the conventional siRNA or the siRNA multi-conjugate linked by cleavable or non-cleavable covalent bond and a cationic gene carrier (Linear PEI, Jet-PEI or DOTAP). The ionic complex is introduced into PBMC (Peripheral Blood Mononuclear Cell) extracted from human blood, followed by quantification of IFN-alpha released from the cell by ELISA. FIG. 9B illustrates that an ionic complex is prepared by using the conventional siRNA or the siRNA multi-conjugate linked by cleavable or non-cleavable covalent bond and the cationic gene carrier Linear PEI, which is intravenously injected into ICR mouse, followed by quantification of IFN-alpha released from blood by ELISA.

EXAMPLES

Mode for Invention

Practical and presently preferred embodiments of the present invention are illustrative as shown in the following Examples.

However, it will be appreciated that those skilled in the art, on consideration of this disclosure, may make modifications and improvements within the spirit and scope of the present invention.

Figure 1A:
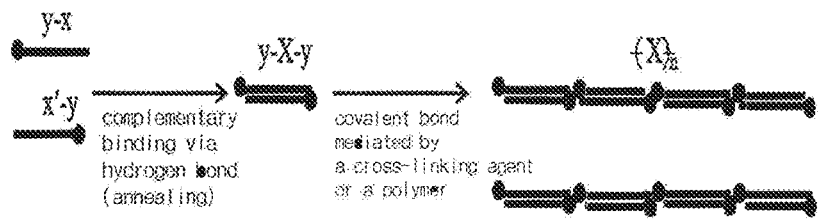
FIGS. 1A-1D illustrate the preparing method of a multi-conjugate of siRNA.
Figure 2A:
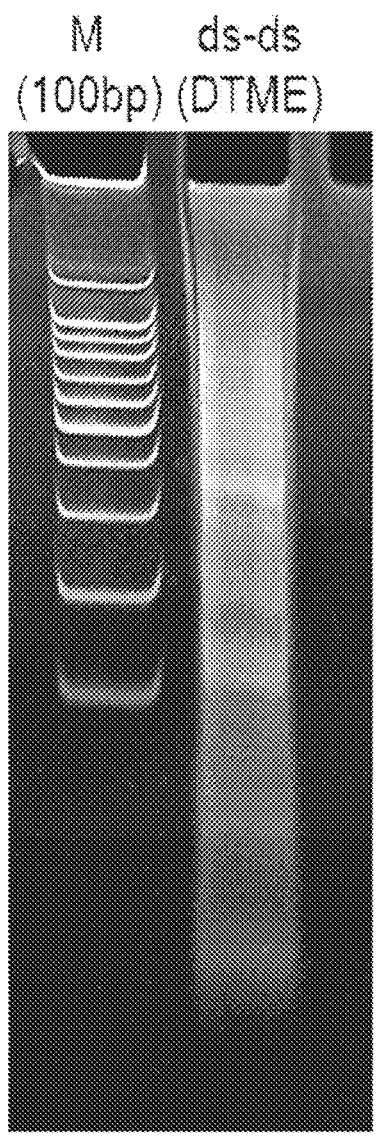
FIGS. 2A-2B illustrate the result of electrophoresis of the multi-conjugate of siRNA. Double-stranded siRNA is prepared by hydrogen bonding between sense strand siRNA and antisense strand siRNA both having the substitution with sulfhydryl group at 3'end. Then, a multi-conjugate of siRNA is prepared by using the cross-linking agent DIME as shown in FIG. 2A or a multi-conjugate of siRNA is prepared by using the cross-linking agent BM(PEG)$_2$ as shown in FIG. 2B (by the method of FIG. 1A).
Figure 2B:
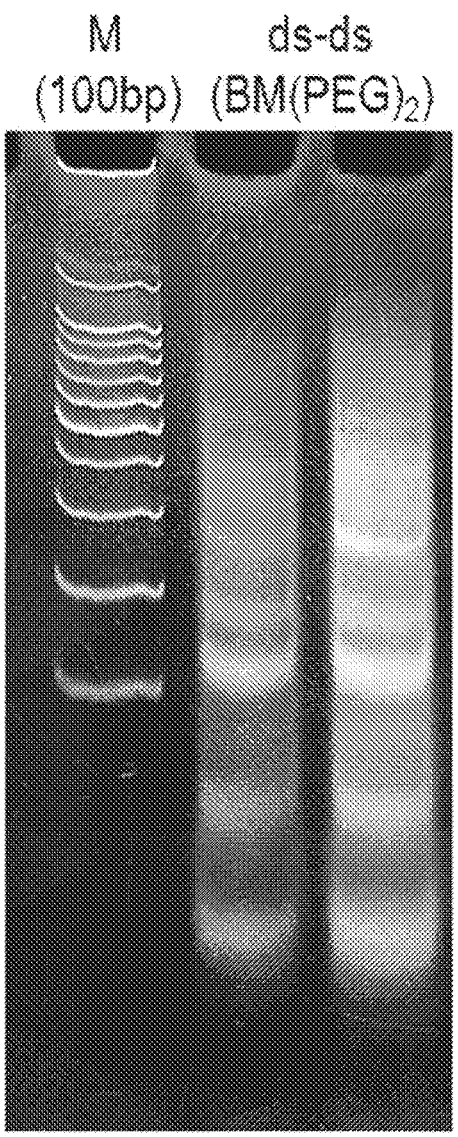

Example 1: Preparation of Double-Stranded siRNA Via Hydrogen Bond of Sense Strand siRNA and Antisense Strand siRNA Having Substitution with Same Functional Group at their Ends and Preparation of Multi-Conjugate of siRNA Using Cross-Linking Agent 100 nmol of sense or antisense strand siRNA having substitution with sulfhydryl group at 3' end was dissolved in 260 µl of 1×PBS, which stood at 37° C. for 1 hour, resulting in double-stranded siRNA. To reduce sulfhydryl group at both ends of the prepared double-stranded siRNA, 22 µl of 25×PBS, 260 µl of 2M DTT (dithiothreitol) solution and 4 µl of 5N NaOH solution (to adjust pH) were added thereto, followed by reaction for 12 hours. Upon completion of the reaction, remaining DTT was eliminated by dialysis and the solution was concentrated to 1 nmol/µl. 25×PBS was added to adjust the final concentration to 5×PBS. The cross-linking agent DTME or BM(PEG)$_2$ was added at the concentration of half the concentration of thiol group, followed by reaction at room temperature for 24 hours. Upon completion of the reaction, remaining foreign materials such as cross-linking agent, etc, were eliminated by dialysis and the solution was concentrated to make the final concentration to 1~2 µg/µl to prepare a siRNA multi-conjugate (see FIG. 1A). The prepared siRNA was confirmed by electrophoresis. (see FIG. 2)

Figure 3A:
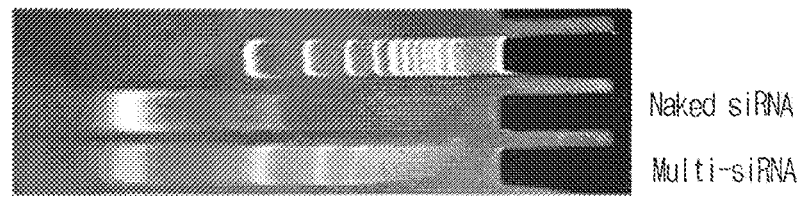
FIG. 3A illustrates the result of electrophoresis of the multi-conjugate of siRNA prepared by using double-stranded siRNA having the substitution with sulfhydryl group at 3' ends of both sense and antisense siRNA.

A multi-conjugate was prepared by direct covalent bonding of double-stranded siRNA mediated by oxidation without using a cross-linking agent. Double-stranded siRNA having substitution with thiol group at 3' ends of sense and antisense strands was treated with DTT by the same manner as described above, followed by dialysis and concentration to make the final concentration of the solution to 1 nmol/µl. DMSO and diamide were added to the above solution to oxidize sulfhydryl, resulting in the formation of disulfide bond. The prepared double-stranded siRNA multi-conjugate was confirmed by electrophoresis (see FIG. 3A).

Figure 3B:
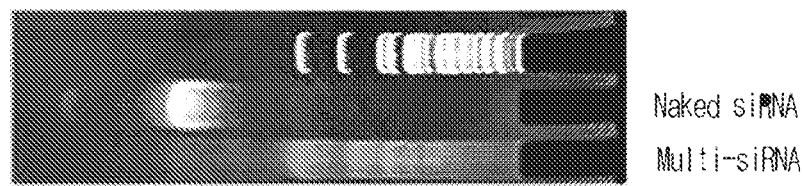
FIG. 3B illustrates the result of electrophoresis of the multi-conjugate of siRNA prepared by complementary binding of dimers produced from sense and antisense siRNA having substitution with sulfhydryl group at 3'end in the presence of a cross-linking agent.
Figure 3C:
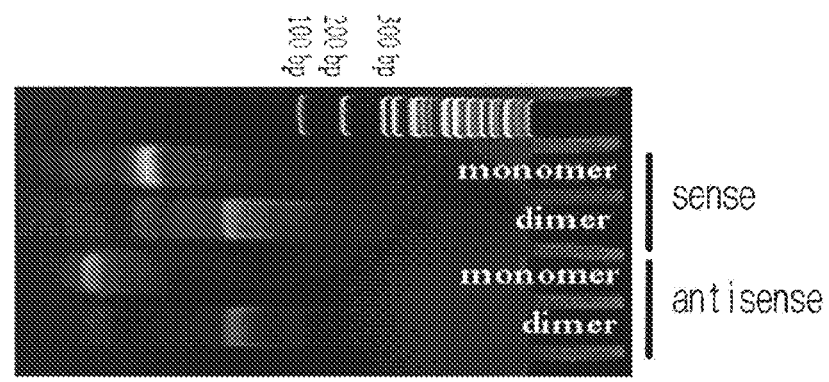
FIGS. 3C-3D illustrate observation of dimer by electrophoresis after preparing the dimer by using sense and antisense siRNA of the dimer in the presence of a cross-linking agent that is capable of linking sense siRNA and antisense siRNA having substitution with sulfhydryl group at 3'end by cleavable covalent bond which is disulfide bond FIG. 3C or by non-cleavable covalent bond FIG. 3D.
Figure 3D:
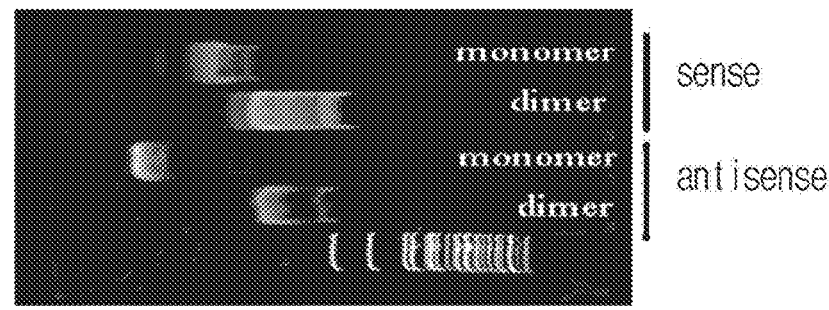

Example 2: Preparation of Dimer of Each Sense Strand siRNA and Antisense Strand siRNA Having the Substitution with Same Functional Group at the End Using Cross-Linking Agent and Preparation of siRNA Multi-Conjugate Via Hydrogen Bond 100 nmol of sense or antisense strand siRNA having the substitution with sulfhydryl group at 3' end was dissolved in 260 µl of DEPC (Diethyl pyrocarbonate) treated deionized water, to which 22 µl of 25×PBS was added. 260 µl of 2M DTT (dithiothreitol) was added thereto and then 4 µl of 5N NaOH was added to adjust pH, followed by reaction for 12 hours. Upon completion of the reaction, remaining DTT was eliminated by dialysis and the solution was concentrated. As a result, sense or antisense strand siRNA having the final concentration of 1 nmol/µl was prepared. 25×PBS was added to adjust the final concentration to 5×PBS. The cross-linking agent DIME or BM(PEG)$_2$ was added thereto at the concentration of half the concentration of thiol group, followed by reaction at room temperature for hours. Upon completion of the reaction, foreign materials such as cross-linking agent, etc, were eliminated by dialysis, and the solution was concentrated to prepare the dimer form of sense or antisense siRNA having the final concentration of 1-2 µg/µl (see FIG. 1B). The dimer prepared by cleavable disulfide bond (see FIG. 3C) or non-cleavable covalent bond (see FIG. 3D) were confirmed by electrophoresis. Equal amount of sense and antisense dimers stood in PBS at 37° C. for 1 hour to induce hydrogen bond. As a result, a siRNA multi-conjugate was prepared and confirmed by electrophoresis (see FIG. 3B).

Example 3: Preparation of Double-Stranded siRNA by Hydrogen Bonding of Sense Strand siRNA and Antisense Strand siRNA Having Different Functional Groups at their Ends and Preparation of siRNA Conjugate Using Cross-Linking Agent Sense strand and antisense strand siRNA having respectively amine group and sulfhydryl group at 3'end were prepared. 100 nmol of each sense and antisense siRNA was dissolved in 260 µl of PBS, which stood at 37° C. for 1 hour, resulting in the preparation of double-stranded siRNA. DTT was treated thereto in order to prepare single-stranded siRNA having sulfhydryl group substituted at the end, followed by dialysis and concentration to make the final concentration of 1 nmol/µl. The cross-linking agent sulfo-SMCC (sulfosuccinimidyl-4-[N-maleimidomethyl]-cyclohexane-1-carboxylate) was added to the prepared double stranded siRNA, followed by reaction for 24 hours to prepare a multi-conjugate of siRNA. Upon completion of the reaction, remaining foreign materials such as cross-linking agent, etc, were eliminated by dialysis and the solution was concentrated to make the final concentration to 1~2 µg/µl (see FIG. 1C).

Example 4: Preparation of Dimer of Each Sense Strand siRNA and Antisense Strand siRNA Having the Substitution with Different Functional Groups at their Ends Using Cross-Linking Agent and Preparation of siRNA Multi-Conjugate Via Hydrogen Bond Sense and antisense siRNA each having amine group and sulfhydryl group at 3' end were linked to make double-stranded siRNA using the cross-linking agent sulfo-SMCC. Single-stranded siRNA having the substitution with sulfhydryl group at the end was treated with DTT, followed by dialysis and concentration until the final concentration reached 1 nmol/µl. Single-stranded siRNA having the substitution with amine group at the end was dissolved in DEPC treated distilled water at the concentration of 1 nmol/µl. Each solution containing sense and antisense having respectively amine group and sulfhydryl group was treated with sulfo-SMCC to prepare sense or antisense dimer. The prepared sense or antisense dimer was mixed in PBS, which stood at 37° C. for 1 hour, resulting in the preparation of a double-stranded siRNA multi-conjugate (see FIG. 1D).

Experimental Example 1: Measurement of GFP Expression

An ionic complex was prepared from the siRNA multi-conjugate (prepared by the method of FIG. 1A) linked by cleavable disulfide bond or non-cleavable covalent bond using the siRNA inhibiting GFP gene, the conventional siRNA, a cross linking agent and linear PEI (polyethyleneimine). The prepared ionic complex was treated to the cancer cell line MDA-MB-435 expressing GFP stably for 5 hours. 48 hours later, GFP expression was quantified with a fluorophotometer.

Figure 4:
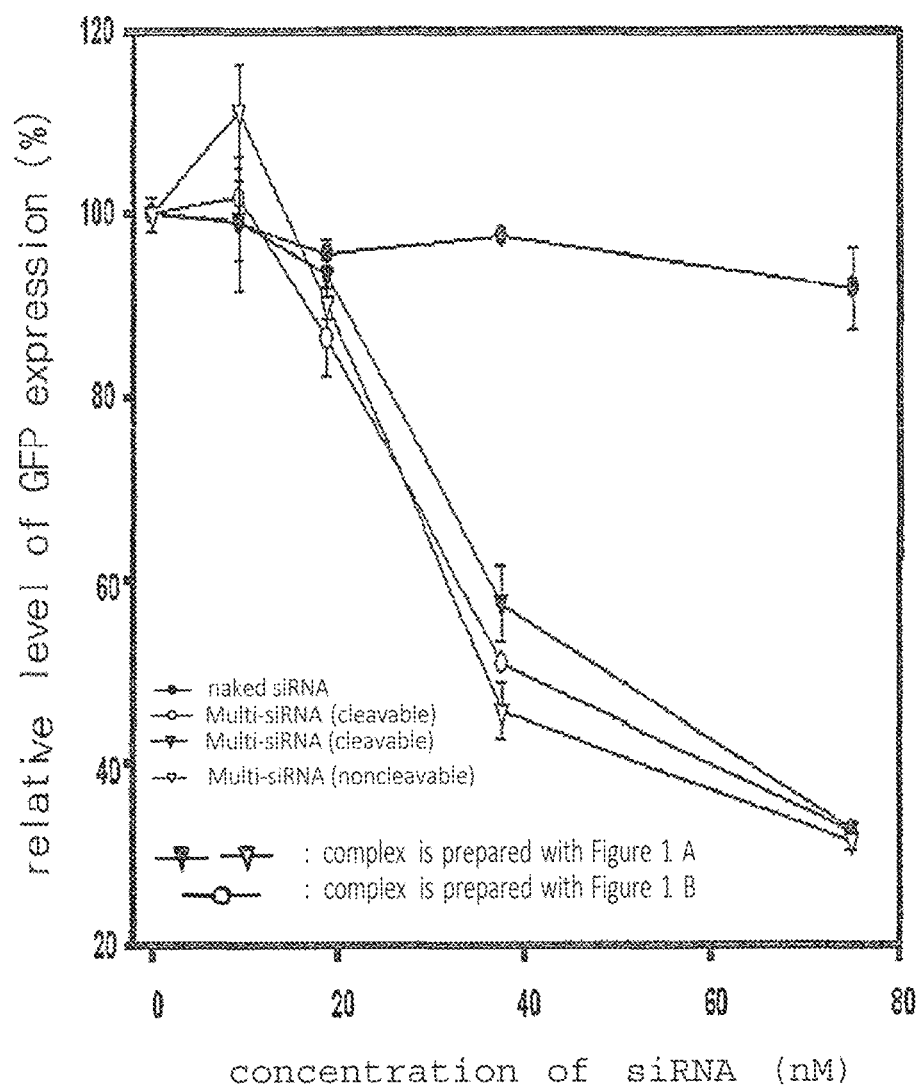
FIG. 4 illustrates that a complex is prepared with the siRNA multi-conjugate to GFP of FIG. 1A and FIG. 1B and the conventional siRNA using the cationic gene carrier linear PEI at NP ratio 20. Then, the complex is treated to the cancer cell line MDA-MB-435 expressing GFP stably, followed by quantification of GFP inhibition.

As a result, the siRNA multi-conjugate of the present invention demonstrated excellent gene delivery efficiency using a cationic gene carrier and excellent target gene inhibition activity, compared with the conventional siRNA (see FIG. 4).

Experimental Example 2: Measurement of Binding Strength with Cationic Gene Carrier and Stability To confirm whether the siRNA multi-conjugate (prepared by the method of FIG. 1B) had excellent binding strength with a cationic gene carrier and could form a stable ionic complex, compared with the conventional siRNA, the present inventors mixed the representative gene carrier Linear PEI and each siRNA to produce each ionic complex. And then, shape and size of each complex were observed by AFM.

Figure 5:
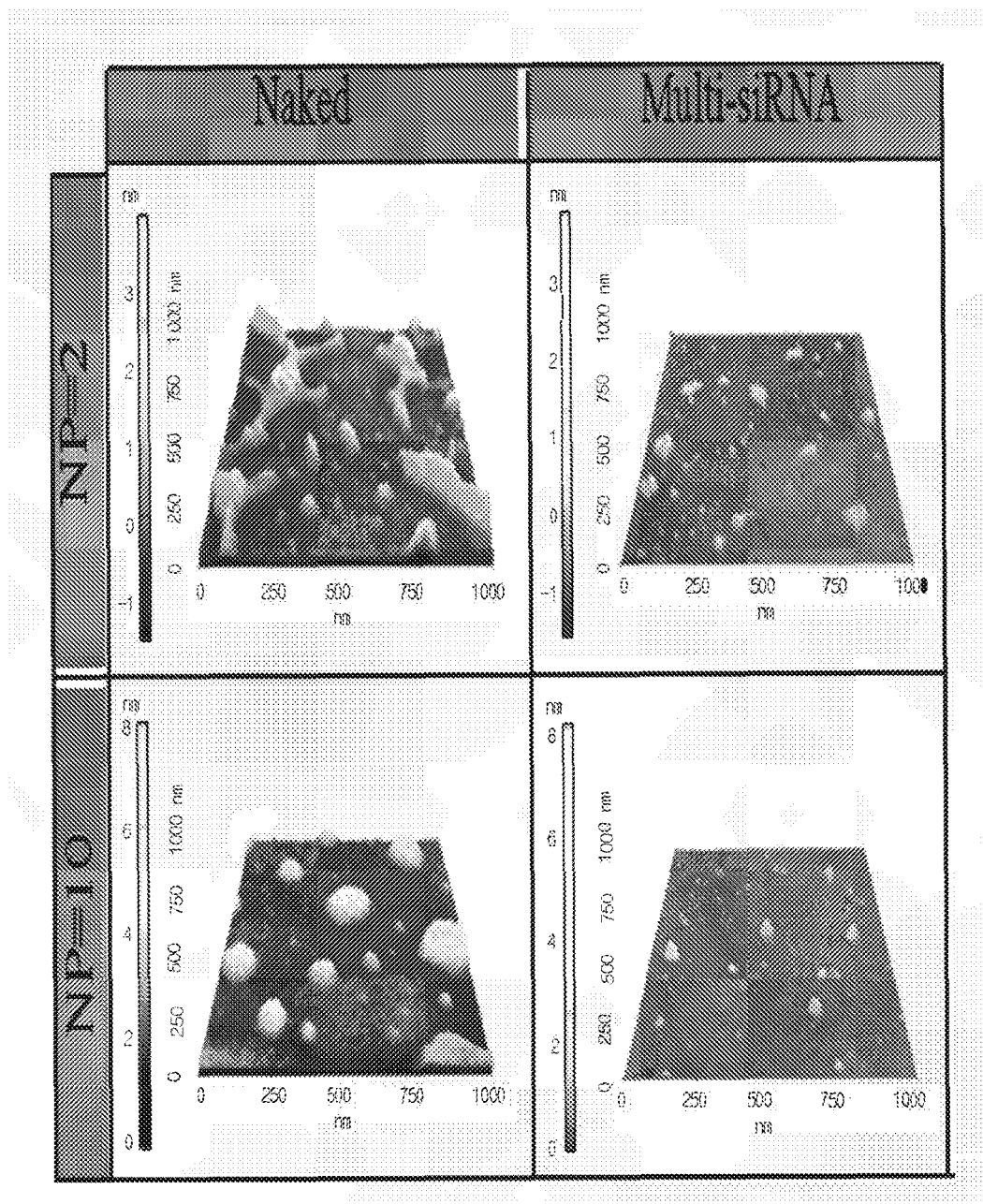
FIG. 5 illustrates that an ionic complex is prepared from the siRNA multi-conjugate (prepared by the method of FIG. 1B) and the conventional siRNA (Naked) using the cationic gene carrier linear PEI at NP ratio 2 and 10, and then the size and shape are observed by atomic force microscopy (AFM).

As a result, the siRNA multi-conjugate of the present invention demonstrated excellent binding strength with a cationic polymer and was capable of forming small but even nano particles, compared with the conventional siRNA (see FIG. 5).

To investigate the amount of the cationic polymer binding to each siRNA, gel retardation assay was performed.

Figure 6:
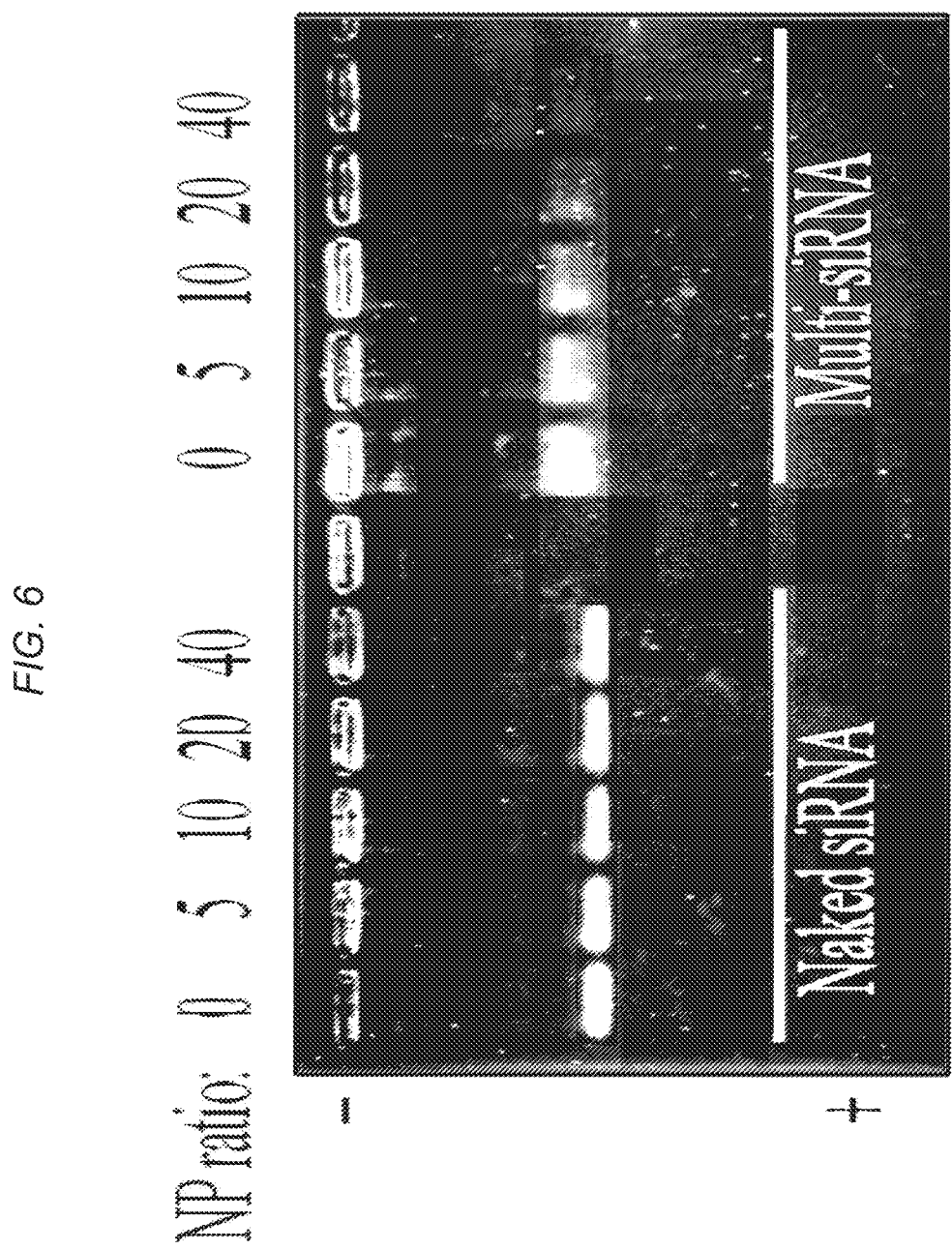
FIG. 6 illustrates that ion complexes are prepared by using the siRNA multi-conjugate (prepared by the method of FIG. 1B) and the conventional siRNA (Naked) using the cationic gene carrier linear PEI over different NP ratios, followed by electrophoresis to observe the ionic complex formation.

As a result, the siRNA multi-conjugate of the present invention had higher charge density than the conventional siRNA, suggesting that the siRNA multi-conjugate of the present invention can form an ionic complex by binding with a cationic polymer even at a low concentration (see FIG. 6).

Experimental Example 3: Investigation of Gene Inhibition Efficiency Using VEGF

An ionic complex was prepared from the siRNA multi-conjugate (prepared by the method of FIG. 1B) linked by cleavable disulfide bond or non-cleavable covalent bond using the siRNA inhibiting VEGF gene, the conventional siRNA, and linear PEI (polyethyleneimine) The prepared ionic complex was treated to PC3 cancer cells for 5 hours. Then VEGF secreted for 21 hours was quantified by ELISA. The experiment was performed over the siRNA concentration (0, 18, 45, and 90 nM) and over the NP ratio (0, 10, 15, and 20), which was the ratio of amine in the cationic carrier to phosphate of nucleotide. To investigate weather intracellular mRNA was reduced selectively, each ionic complex was treated to cancer cells for 5 hours. 18 hours later, RNA was extracted, followed by PCR to measure the level of intracellular VEGF mRNA.

Figure 7A:
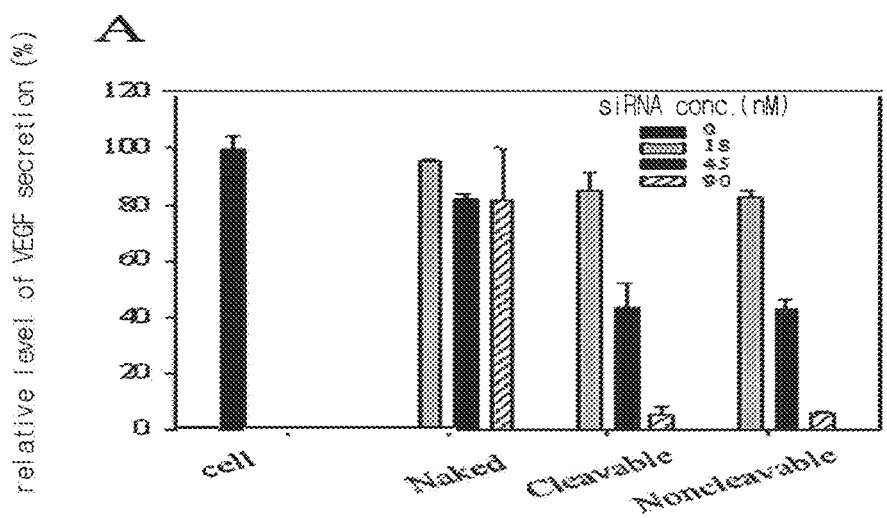
FIGS. 7A-7C illustrate that a siRNA multi-conjugate linked by cleavable disulfide bond or non-cleavable covalent bond is prepared by the method of FIG. 1B using siRNA inhibiting VEGF (Vascular endothelial growth factor), followed by comparison of gene inhibition efficiency with the conventional siRNA (Naked). Linear PEI is used as a gene carrier. Gene inhibition efficiency is measured over the concentration of siRNA as shown in FIG. 7A and over the NP ratio as shown in FIG. 7B by ELISA, by which VEGF level is quantified.
Figure 7B:
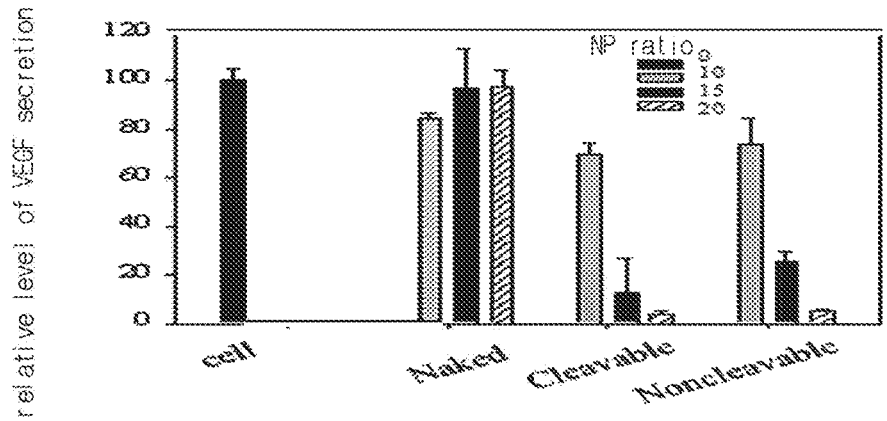
Figure 7C:
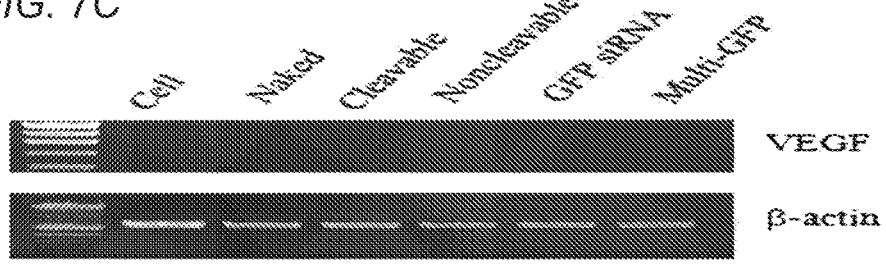

As a result, the siRNA multi-conjugate of the present invention could form a stable and even ionic complex with a cationic polymer, compared with the conventional siRNA, and demonstrated excellent gene delivery efficiency and target gene inhibition activity (see FIG. 7).

Experimental Example 4: Investigation of VEGF Inhibition Efficiency

Figure 1B:
Figure 1C:
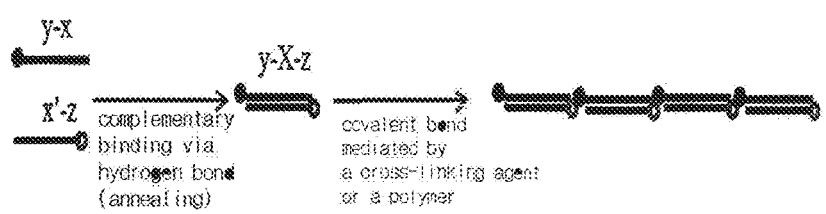
Figure 1D:
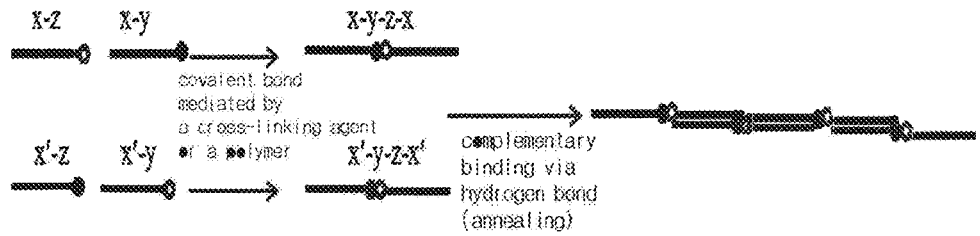

Electrophoresis was performed with the VEGF siRNA multi-conjugate prepared by the method of FIG. 1B, and siRNA was sorted over the size by gel separation method, followed by electrophoresis to confirm thereof. Each siRNA was mixed with Linear PEI to form a complex. 90 nM of the siRNA conjugate was treated to PC3 cell, and then VEGF gene inhibition effect was measured.

Figure 8A:
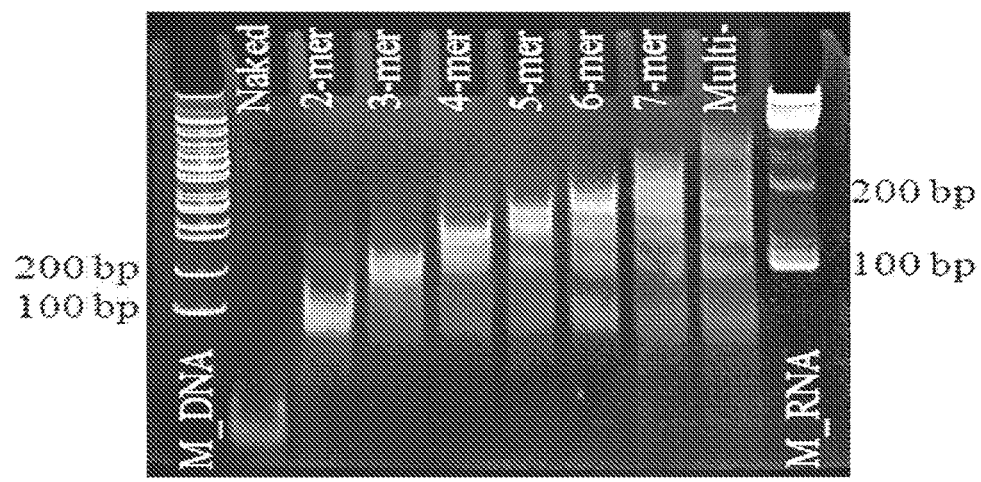
FIG. 8A illustrates that a siRNA multi-conjugate is prepared by the method of FIG. 1B and each siRNA is separated, followed by electrophoresis.
Figure 8B:
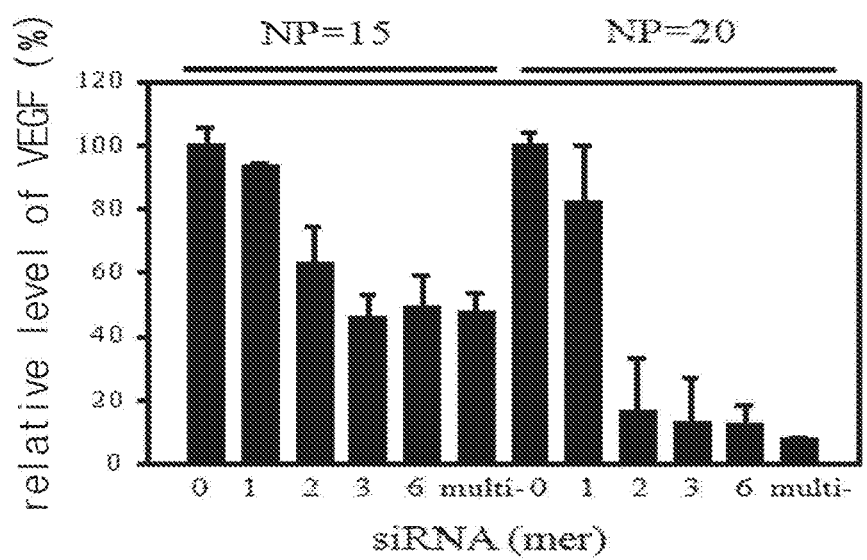
FIG. 8B illustrates that gene inhibition efficiency of each separated multi-conjugate is compared by quantifying VEGF by ELISA.

As a result, as molecular weight of the siRNA multi-conjugate increased, charge density was increased, suggesting the improvement of gene delivery efficiency using a cationic polymer (see FIG. 8).

Experimental Example 5: Induction of Immune Response by siRNA Multi-Conjugate

To investigate immune response induction capacity of the siRNA multi-conjugate prepared by the method of FIG. 1B, peripheral blood mononuclear cells (PBMC) were separated from human blood by using Fisher lymphocyte separation medium. An ionic complex was prepared from the conventional VEGF siRNA or the siRNA multi-conjugate linked by cleavable disulfide bond or non-cleavable covalent bond by using the cationic gene carrier linear PEI, jet PEI or DOTAP.

The siRNA complex was treated to PBMC at the final concentration of 360 nM for 24 hours. INF-alpha level in the supernatant was measured by ELISA.

Figure 9A:
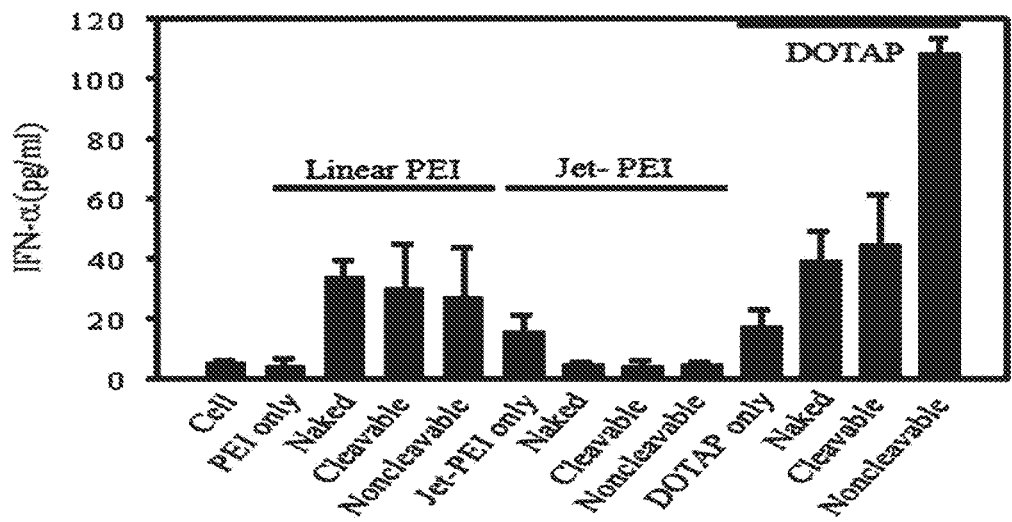
FIGS. 9A-9B illustrate the IFN-alpha induction by the siRNA multi-conjugate prepared by the method of FIG. 1B.

As a result, the siRNA multi-conjugate of the present invention did not induce INF-alpha significantly, compared with the conventional siRNA. In particular, the siRNA multi-conjugate prepared by disulfide bond demonstrated similar INF-alpha induction to the conventional siRNA (see FIG. 9A).

To confirm whether the prepared siRNA multi-conjugate could induce INF-alpha secretion in mouse, 40 μl of the conventional siRNA or the siRNA multi-conjugate prepared by cleavable disulfide bond or non-cleavable covalent bond was mixed with the cationic gene carrier linear PEI to form an ionic complex, which was injected intravenously into ICR mouse at 7 weeks. After 6 hours of the treatment, blood was taken from the heart of the mouse, followed by ELISA to quantify blood siRNA.

Figure 9B:
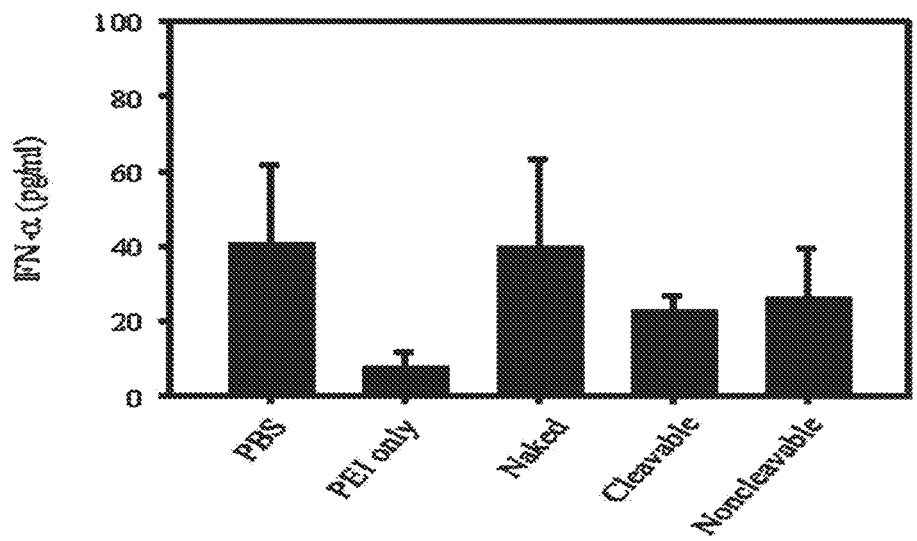

As a result, compared with the conventional siRNA, the siRNA multi-conjugate of the present invention did not induce INF-alpha secretion significantly in the animal model (see FIG. 9B).

INDUSTRIAL APPLICABILITY

The siRNA multi-conjugate of the present invention can be applied in medicinal field including gene therapy owing to the improved gene delivery efficiency and thereby further contributes to the advancement of national industry by realizing diverse applications thereof in related fields.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A purified single-stranded homodimeric RNA having, the structure:

—••—, or —•○—, wherein each ——— is a subunit of RNA having 15-50 nucleotides;

wherein each of the subunits is identical;

wherein and • and ○ are distinct functional groups mediating a bond between the subunits; and wherein the bond is a non-cleavable bond.

2. The purified single-stranded homodimeric RNA of claim 1, wherein the subunits are bonded 3' end to 3' end.

3. The purified single-stranded homodimeric RNA of claim 1, wherein the subunits are bonded 5' end to 5' end.

4. The purified single-stranded homodimeric RNA of claim 1, wherein the subunits are bonded 3' end to 5' end.

5. The purified single-stranded homodimeric RNA of claim 1, wherein subunits are sense or antisense siRNAs.

6. The purified single-stranded homodimeric RNA of claim 1, wherein the subunits are complementary to c-myc, c-myb, c-fos, c-jun, bcl-2, VEGF, VEGF-B, VEGF-c, VEGF-D, or PIGF mRNA.

7. The purified single-stranded homodimeric RNA of claim 1, wherein each of the subunits has 15-29 nucleotides.

8. The purified single-stranded homodimeric RNA of claim 1, wherein the non-cleavable bond is an amide bond or a urethane bond.

9. The purified single-stranded homodimeric RNA of claim 8, wherein the subunits are bonded 3' end to 3' end, or 5' end to 5' end.

10. A method of synthesizing a purified single-stranded homodimeric RNA according to claim 2, the method comprising covalently bonding ——• and •——, or ——• and ○——, thereby synthesizing the purified single stranded homodimeric RNA, wherein the bond is a non-cleavable bond.

* * * * *